(12) United States Patent
Tsutsui et al.

(10) Patent No.: US 11,307,161 B2
(45) Date of Patent: Apr. 19, 2022

(54) FLOW PASSAGE

(71) Applicant: Aipore Inc., Tokyo (JP)

(72) Inventors: Makusu Tsutsui, Suita (JP); Kazumichi Yokota, Suita (JP); Akihide Arima, Suita (JP); Wataru Tonomura, Suita (JP); Masateru Taniguchi, Suita (JP); Takashi Washio, Suita (JP); Tomoji Kawai, Suita (JP)

(73) Assignee: Aipore Inc., Tokyo (JP)

( * ) Notice: Subject to any disclaimer, the term of this patent is extended or adjusted under 35 U.S.C. 154(b) by 0 days.

(21) Appl. No.: 17/258,623

(22) PCT Filed: Jul. 10, 2019

(86) PCT No.: PCT/JP2019/027366
§ 371 (c)(1),
(2) Date: Jan. 7, 2021

(87) PCT Pub. No.: WO2020/013235
PCT Pub. Date: Jan. 16, 2020

(65) Prior Publication Data
US 2021/0270762 A1    Sep. 2, 2021

(30) Foreign Application Priority Data
Jul. 11, 2018    (JP) .............................. JP2018-131885

(51) Int. Cl.
*G01N 27/22* (2006.01)
*B82Y 15/00* (2011.01)

(52) U.S. Cl.
CPC ............ *G01N 27/226* (2013.01); *B82Y 15/00* (2013.01)

(58) Field of Classification Search
CPC . G01N 27/226; G01N 33/48721; B82Y 15/00
See application file for complete search history.

(56) References Cited

U.S. PATENT DOCUMENTS

2013/0270521 A1*  10/2013  Peng ................ G01N 33/48721
257/29
2014/0183040 A1    7/2014  Kawai et al.
(Continued)

FOREIGN PATENT DOCUMENTS

JP      2014-126554 A    7/2014
JP      2016-197077 A    11/2016
(Continued)

OTHER PUBLICATIONS

International Preliminary Report on Patentability for PCT Application No. PCT/JP2019/027366 dated Jan. 21, 2021, 7 pages.
(Continued)

*Primary Examiner* — Alvaro E Fortich
(74) *Attorney, Agent, or Firm* — Bret E. Field; Bozicevic, Field & Francis LLP

(57) ABSTRACT

It is an object to improve detection accuracy of an object as compared with prior arts. A flow passage (10) provided in a detection device (10) includes a substrate (1) and a covering member (2) provided at a position corresponding to the substrate (1). A covering member opening (HL2) of the covering member (2) is provided such that a substrate opening (HL1) of the substrate (1) is not covered with the covering member (2). The covering member (2) is arranged onto the substrate (1) such that a substrate capacitance and a covering member capacitance are connected in series. The covering member capacitance is lower than the substrate capacitance.

18 Claims, 11 Drawing Sheets

(56) References Cited

U.S. PATENT DOCUMENTS

| | | | |
|---|---|---|---|
| 2014/0221249 A1* | 8/2014 | Chen | G01N 33/48721 |
| | | | 506/12 |
| 2015/0369776 A1* | 12/2015 | Rosenstein | B82Y 5/00 |
| | | | 204/452 |
| 2016/0231307 A1 | 8/2016 | Xie | |

FOREIGN PATENT DOCUMENTS

| | | | | |
|---|---|---|---|---|
| JP | 2018-510329 A | 4/2018 | | |
| WO | WO2015083767 A1 | 6/2015 | | |
| WO | WO-2018136497 A1 * | 7/2018 | | G03F 7/167 |

OTHER PUBLICATIONS

Rosenstein et al.. Integrated nanopore sensing platform with sub-microsecond temporal resolution, Nat Methods, Mar. 18, 2012; 9(5):487-92.
Goto et al., Integrated solid-state nanopore platform for nanopore fabrication via dielectric breakdown, DNA-speed deceleration and noise reduction, Sci Rep, Aug. 8, 2016; 6:31324.
Lee et al., A Low-Noise Solid-State Nanopore Platform Based on a Highly Insulating Substrate, Sci Rep, Dec. 2014,4(1):7448.
Extended European Search Report for European Application No. 19834886.4 dated Jul. 21, 2021, 8 pages.

* cited by examiner

FLOW PASSAGE

FIELD OF THE INVENTION

An aspect of the present invention relates to a flow passage provided in a nanopore sensor.

BACKGROUND OF THE INVENTION

In recent years, a device (nanopore sensor) for detecting an object using a nanopore (a nanoscale pore) has been developed. The nanopore sensor can detect the object by measuring a change of ionic current, which occurs when the object passes through the nanopore (see, for example, Patent Literature 1).

CITATION LIST

Patent Literatures

[Patent Literature 1] Japanese Patent Application Publication No. 2016-197077A
[Patent Literature 2] Japanese Patent Application Publication No. 2014-126554A

SUMMARY OF THE INVENTION

Technical Problem

However, as will be described later, there is still room for improvement of a device for increasing detection accuracy of an object in a nanopore sensor. An object of one aspect of the present invention is to improve the detection accuracy of the object as compared with the prior arts.

Solution to Problem

In order to solve the above problems, a flow passage according to an aspect of the present invention is a flow passage provided in a nanopore sensor, the flow passage comprising: a substrate; and a covering member provided at a position corresponding to the substrate, wherein the substrate comprises a substrate opening that penetrates the substrate in a first direction, the first direction being a thickness direction of each of the substrate and the covering member, wherein the covering member comprises a covering member opening that penetrates the covering member in the first direction, wherein the covering member opening is provided such that the substrate opening is not covered with the covering member, wherein the covering member is arranged to the substrate such that a substrate capacitance and a covering member capacitance are connected in series, the substrate capacitance being a capacitance of the substrate and the covering member capacitance being a capacitance of the covering member, and wherein the covering member capacitance is lower than the substrate capacitance.

Advantageous Effects of Invention

According to an aspect of the present invention, it is possible to improve detection accuracy of an object as compared with the prior arts.

DETAILED DESCRIPTION OF THE INVENTION

First Embodiment

Figure 1:
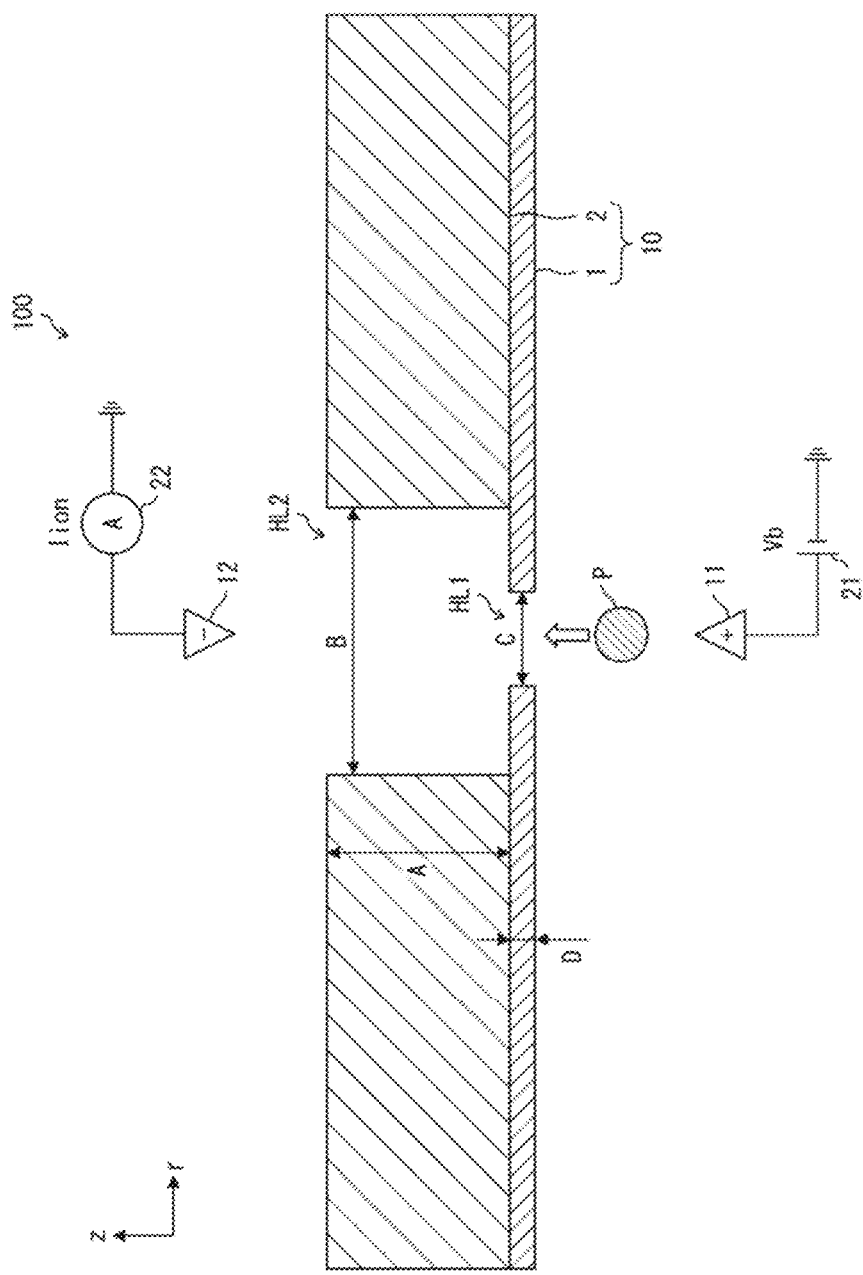
FIG. 1 is a view for explaining a configuration of a detection device according to a first embodiment.

A detection device 100 (nanopore sensor) according to a first embodiment will be described below. For convenience of explanation, in each of the following embodiments, the same reference numerals are labeled to members having the same functions as those described in the first embodiment, and descriptions thereof will not be repeated.

In the present specification, the same matters as those of known arts will be omitted as appropriate. It may be understood that the matters that have omitted the descriptions are the same as those of the known arts. For example, see Patent Literature 2 for the basic principle of the nanopore sensor.

(Configuration of Detection Device 100)

FIG. 1 is a view for explaining a configuration of the detection device 100. The detection device 100 is an example of a nanopore sensor for detecting a particle P (object) as a sample. In the example below, the particle P is any nanoparticle. Therefore, for convenience of explanation, the shape of the particle P is illustrated as a sphere. However, the shape of the particle P is not limited to the sphere. The shape of the particle P may be any shape as long as the particle P can pass through a flow passage 10 as described below.

Figure 2:
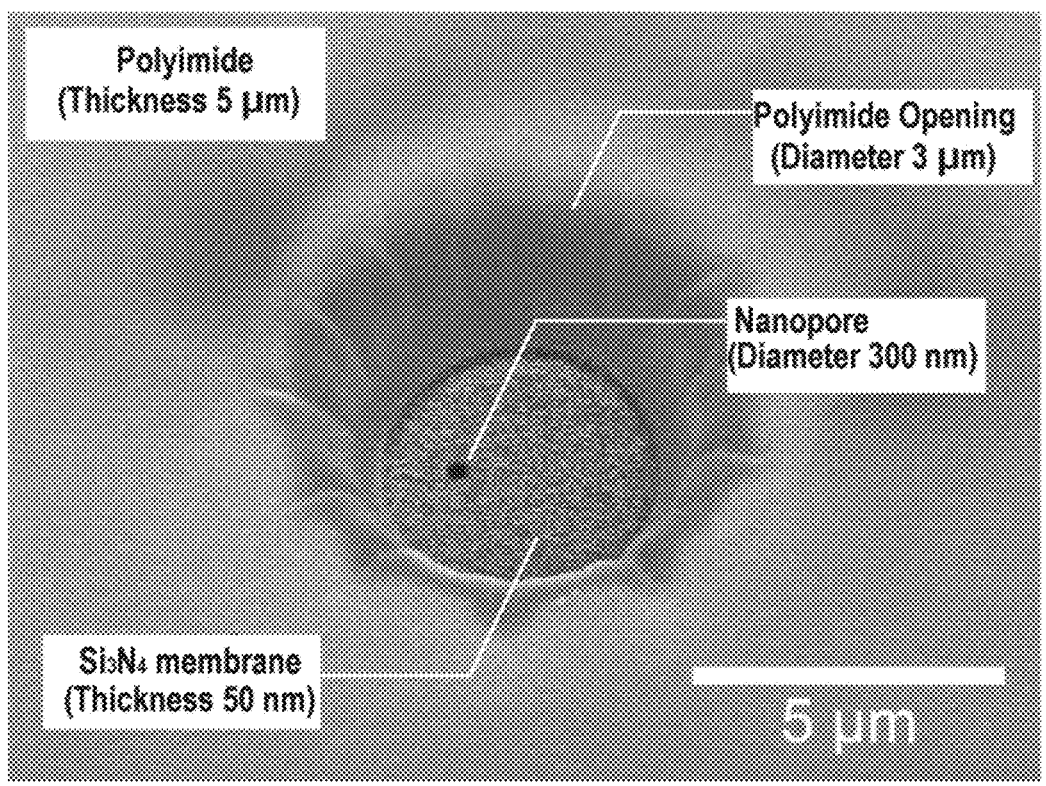
FIG. 2 is a view showing an example of an SEM image of a flow passage.

Further, it should be noted that FIG. 1 is a view schematically showing a configuration example of the detection device 100. For example, in FIG. 1, dimensions of each member are not necessarily drawn according to its actual scale. Further, the position of each member may not be limited to the arrangement as shown in FIG. 1. For example, as shown in FIG. 2 as described later, a central axis of HL1 (as described later) and a central axis of HL2 (as described later) may not necessarily coincide with each other. The same is true for FIG. 3 and the like as described later.

The detection device 100 includes: a flow passage 10; a first electrode 11; a second electrode 12; a voltage source 21;

and an ammeter 22. The first electrode 11 and the second electrode 12 are arranged to face each other so as to form a pair of electrodes. In the embodiment of FIG. 1, the first electrode 11 and the second electrode 12 are separated from each other in a z direction (as described later). As the first electrode 11 and the second electrode 12, for example, silver/silver chloride (Ag/AgCl) electrodes can be used.

In the embodiment of FIG. 1, the first electrode 11 and the second electrode 12 function as a positive electrode and a negative electrode, respectively. More particularly, a voltage source 21 applies a voltage having a predetermined magnitude (hereinafter, Vb) to the first electrode 11. A positive side of the voltage source 21 is connected to the first electrode 11. A negative side of the voltage source 21 is grounded. As an example, the Vb is 0.1V. One terminal of the ammeter 22 is connected to the second electrode 12. The other terminal of the ammeter 22 is grounded. The ammeter 22 measures an ion current (hereinafter, Iion) generated when the particle P passes through the flow passage 10.

According to the configuration of FIG. 1, the Vb is applied between the first electrode 11 and the second electrode 12. That is, an electric field can be formed in the z direction. The electric field can move the particle P in the z direction. For example, the positively charged particle P can be moved from the side of the first electrode 11 to the side of the second electrode 12.

The flow passage 10 is arranged so as to be interposed between the first electrode 11 and the second electrode 12 in the z direction. The flow passage 10 includes a substrate 1 and a covering member 2. As an example, both of the substrate 1 and the covering member 2 are insulating materials. Therefore, the flow passage 10 may be referred to as an insulating structure. As an example, the substrate 1 is a thin film of $Si_3N_4$ ($Si_3N_4$ membrane). The covering member 2 is provided at a position corresponding to the substrate 1. In the first embodiment, the covering member 2 is deposited on the substrate 1 so as to cover a part of the substrate 1. As an example, the covering member 2 covers a part of two surfaces (more strictly, main surfaces) of the substrate 1, which is opposed to the second electrode 12. As an example, the covering member 2 is a layer of polyimide (polyimide layer). The covering member 2 is also referred to as a covering layer.

As used herein, a surface opposing to the second electrode 12, of the two surfaces of the substrate 1, refers to "a first surface of the substrate 1." Hereinafter, for convenience of explanation, the first surface of the substrate 1 is also referred to as "an upper surface (a front surface) of the substrate 1". Further, a surface opposing to the first electrode 11, of the two surfaces of the substrate 1, is referred to as "a second surface of the substrate 1". The second surface of the substrate 1 is also referred to as "a lower surface (a back surface) of the substrate 1". As an example, the lower surface of the substrate 1 is provided with a support member (not shown in FIG. 1) for supporting the substrate 1 (also see a fourth embodiment as described later).

The substrate 1 includes a circular opening (hereinafter, HL1) that penetrates the substrate 1 in the z direction. The HL1 defines an internal space of the substrate 1 (hereinafter, a first internal space). In the example of FIG. 1, the first internal space is a cylindrical internal space. Therefore, the shape of the HL1 as viewed from the z direction (referred to as "planar shape of HL1" for convenience) is circular. The HL1 may be referred to as a substrate opening. The HL1 is also called nanopore.

The HL1 is formed such that the particle P can pass through the HL1. Therefore, a diameter of the HL1 (C in FIG. 1) is set to be larger than a diameter of the particle P (hereinafter, dps). As an example, the C is 300 nm and the dps is 100 nm. As used herein, the C is also appropriately referred to as "dpore". The D in FIG. 1 represents a thickness of the substrate 1. The D may be referred to as a depth (height) of the HL1. As an example, the D is equal to 50 nm.

Here, a value of "D/C" (depth/diameter) is referred to as an aspect ratio of the nanopore. The aspect ratio of the nanopore is not particularly limited. Here, the nanopore having a lower aspect ratio (nanopore having a relatively low depth relative to a predetermined diameter) is referred to as a lower aspect ratio nanopore. On the other hand, a nanopore having a higher aspect ratio (nanopore having a relatively high depth relative to a predetermined diameter) is referred to as a higher aspect ratio nanopore.

The use of the lower aspect ratio nanopore results in a complex waveform of an ion current as compared with a case where the higher aspect ratio nanopore is used. Therefore, it is known that the use of the lower aspect ratio nanopore can allow more diverse information on the particle P (e.g., information for specifying the shape of the particle P) to be obtained. Therefore, the first embodiment mainly illustrates the case where the HL1 is the lower aspect ratio nanopore.

The covering member 2 includes an opening (hereinafter, HL2) that penetrates the covering member 2 in the z direction. The HL2 defines an internal space (hereinafter, referred to as a second internal space) of the covering member 2. In the embodiment of FIG. 1, the second internal space is also a cylindrical internal space as with the first internal space. Therefore, the shape of HL2 as viewed from the z direction (referred to as a "planar shape of HL2" for convenience) is circular as with the planar shape of the HL1. The HL2 may be referred to as a covering member opening. The HL2 in the first embodiment may be referred to as a polyimide opening.

The HL2 is formed such that the covering member 2 does not cover the HL1. More particularly, the HL2 is formed so as to include the entire HL1 (so as to overlap with the HL1 as much as possible) as viewed from the z direction. Therefore, a diameter of the HL2 (B in FIG. 1) is set to be sufficiently larger than that of the C. As an example, the B is 3 μm. The A of FIG. 1 shows a thickness of the covering member 2. The A may be referred to as a depth (height) of the HL2. As an example, the A is 5 μm. Thus, the A is sufficiently larger than the D. The HL2 is also called a micropore.

As described above, the HL1 and the HL2 are formed in the flow passage 10. The HL1 and the HL2 define a movement path of the particle P between the electrode pairs (first electrode 11 and second electrode 12). The substrate 1 and the covering member 2 are formed so as to surround a part of the movement path.

When moving the particle P, the first interior space and the second interior space are filled with a medium (not shown). The medium is, for example, an aqueous solution in which an electrolyte is dissolved. Therefore, as shown in Patent Literature 2, the movement of the particle P can be controlled by the electric field and the electroosmotic flow. As described above, the detection device 100 has a function as a control device for controlling the movement of the particle P.

In FIG. 1, the thickness direction of each of the substrate 1 and the covering member 2 is represented as the z direction. The z direction may be referred to as a first direction. The z direction can also be expressed as a depth direction of each of the HL1 and the HL2. Further, the z direction can also be expressed as a normal direction of each of the main surfaces of the substrate 1 and the covering member 2.

On the other hand, radial directions of the HL1 and the HL2 are referred to as r directions. The r direction is orthogonal to the z direction. The r direction may be directed to any direction on a plane (xy plane) perpendicular to the z direction.

The above B (the diameter of the HL2) is more strictly defined as "a maximum length of the HL2 in a direction perpendicular to the z direction". Similarly, the above C (the diameter of the HL1) is more strictly defined as "a maximum length of the HL1 in the direction perpendicular to the z direction". Therefore, the planar shape of the HL1 and the planar shape of the HL2 are not necessarily limited to a circle. For example, the planar shape may be an ellipse or a polygon (e.g., a quadrangle). Further, the three-dimensional shape of each of the first internal space and the second internal space is not necessarily limited to a cylindrical shape (circular pillar shape). For example, the shape may be a truncated cone or a truncated pyramid.

FIG. 2 shows an example of an SEM (Scanning Electron Microscope) image of the flow passage 10. The dimensions of each portion as shown in FIG. 2 are as in the above examples A to D.

(Configuration of Detection Device 100*r* as Comparative Example)

Figure 3:
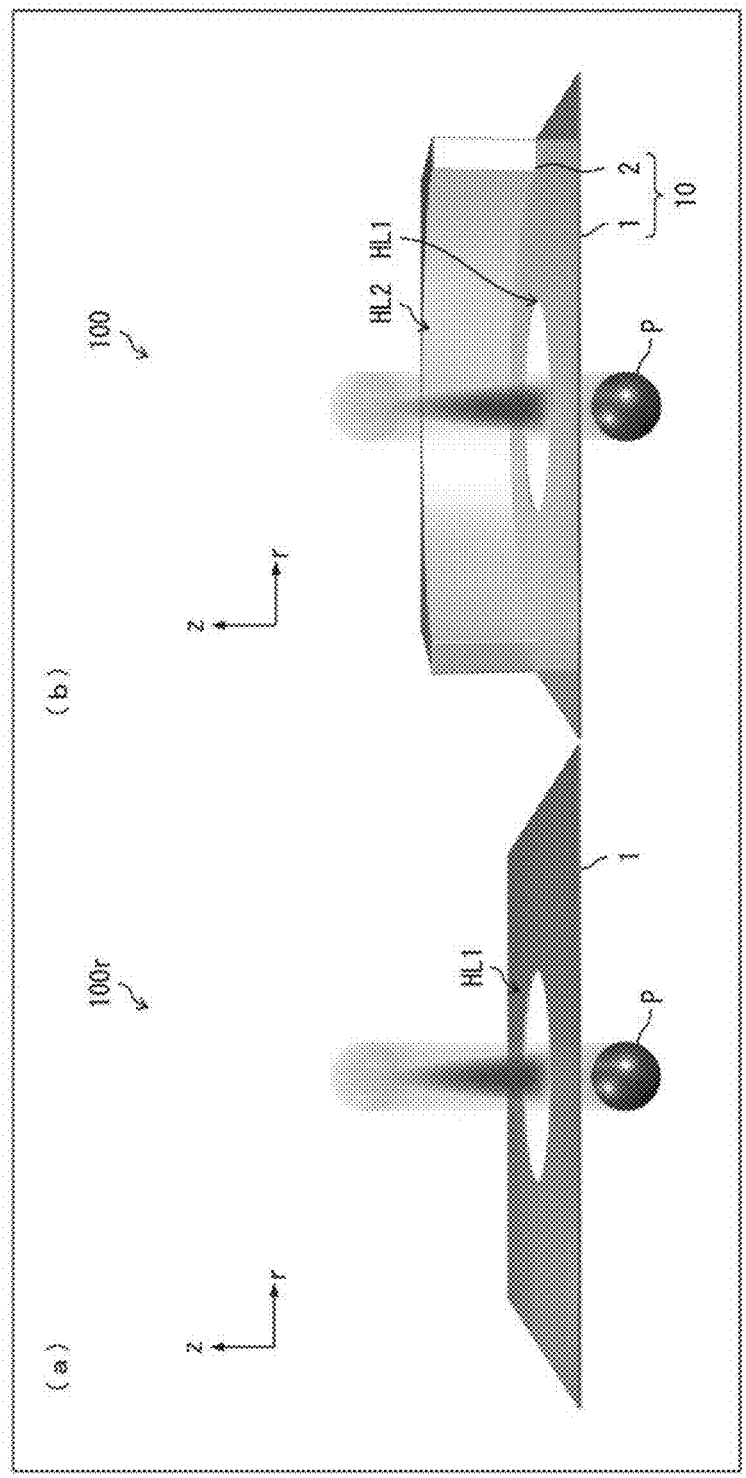
FIGS. 3 (a) and 3 (b) are views for explaining a difference between configurations of a detection device of Comparative Example and a detection device of a first embodiment.

Next, for comparison with the detection device 100, a detection device (hereinafter, referred to as a detection device 100*r*) as a comparative example will be considered. The detection device 100*r* is a configuration example of the conventional nanopore sensors. FIG. 3 is a view for explaining a difference between the configurations of the detection device 100*r* and the detection device 100. In FIG. 3 (*b*), the configurations of the flow passage 10 and its periphery in the detection device 100 are three-dimensionally illustrated.

FIG. 3 (*a*) is a view paired with FIG. 3 (*b*). As shown in FIG. 3 (*a*), the detection device 100*r* has a structure where the covering member 2 is removed from the detection device 100. That is, the detection device 100*r* corresponds to a case set as A=B=0 in the detection device 100. In the detection device 100*r*, unlike the detection device 100, the flow passage is composed of only the substrate 1.

(Observation of Waveform of Ion Current)

The present inventors (hereinafter, simply referred to as the inventors) observed a change of Iion over time for each of the detection device 100*r* and the detection device 100. As the particle P, a carboxy-modified polystyrene nanoparticle was selected. As the medium, an aqueous solution obtained by diluting ultrapure water with a predetermined diluent was used. In the following example, 0.4×PBS (Phosphor Saline Buffer) was used as a diluent. In addition, the dimensions and materials of each portion are as in the above example unless otherwise specified. Therefore, the C (dpore) is equal to 300 nm and the dps is equal to 100 nm. The change of Iion over time was recorded with a sampling rate set to 1 MHz.

<Confirmed Effect 1: Reduction of Current Noise>

Figure 4:
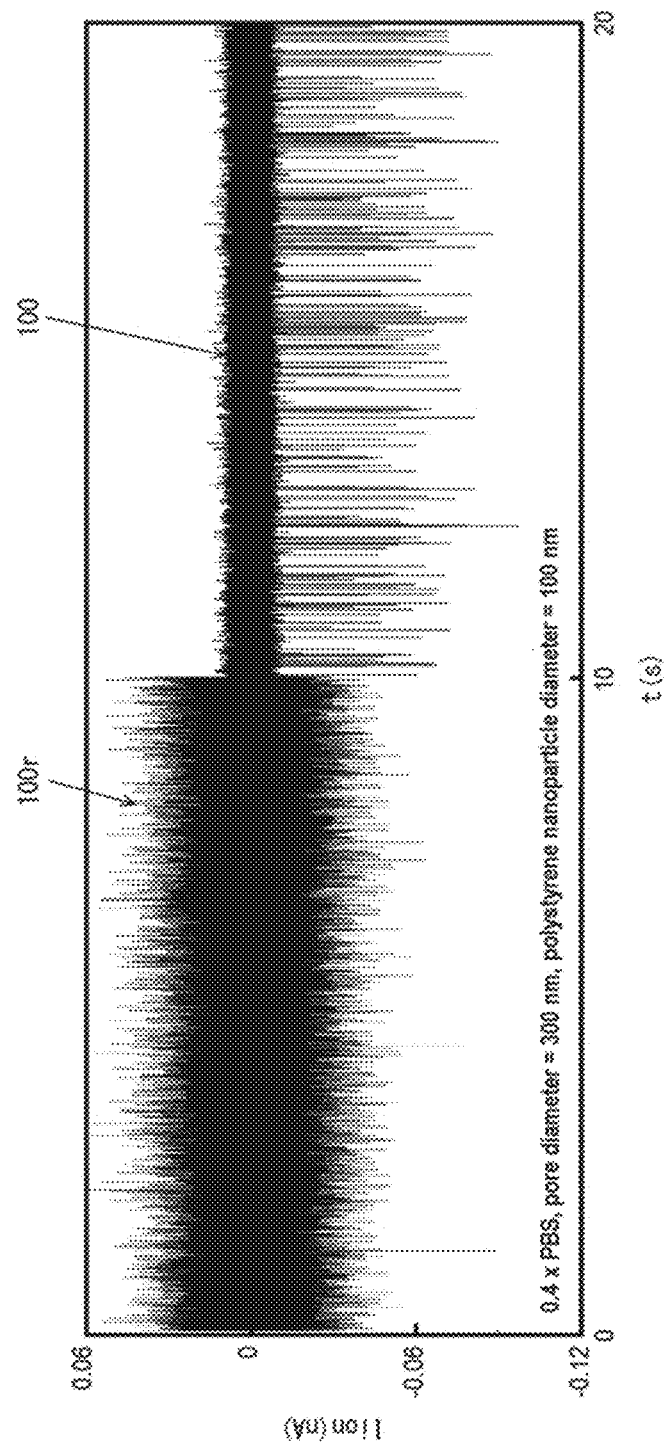
FIG. 4 is a view showing a change of an ion current over time, obtained in each of a detection device of Comparative Example and a detection device of a first embodiment.

FIG. 4 is a graph showing a change of Iion (waveform of Iion) over time, which is obtained by each of the detection device 100*r* and the detection device 100. In the graph of FIG. 4, the horizontal axis is t (time) (unit: s (second)), and the vertical axis is Iion (unit: nA). In both of the detection device 100*r* and the detection device 100, the ion current is blocked by the particle P when one particle P passes through the flow passage (more specifically, the first internal space). Therefore, when one particle P passes through the flow passage, a decrease in Iion (negative pulse of Iion) is observed.

However, as shown in FIG. 4, it was confirmed that in the case of the detection device 100*r*, the noise (current noise) of Iion is sufficiently larger than that in the case of the detection device 100. That is, it was confirmed that by applying the configuration of the detection device 100 (more specifically, the flow passage 10), the current noise can be sufficiently reduced as compared with the detection device 100*r*. Specifically, it was confirmed that in the case of the detection device 100, the current noise was reduced to about ¼ (RMS value) as compared with the case of the detection device 100*r*.

<Confirmed Effect 2: Improvement of Response Rate of Ionic Current>

Subsequently, the inventors examined a response rate of Iion for each of the detection device 100*r* and the detection device 100. The inventors compared one pulse waveform of Iion for each of the detection device 100*r* and the detection device 100. In the following experiments, 0.1×PBS was used as a diluent. Further, the C (dpore) was set to 1200 nm. Then, the value of dps was varied, and the pulse waveform of the Iion (hereinafter, simply referred to as the pulse waveform) was observed.

Figure 5:
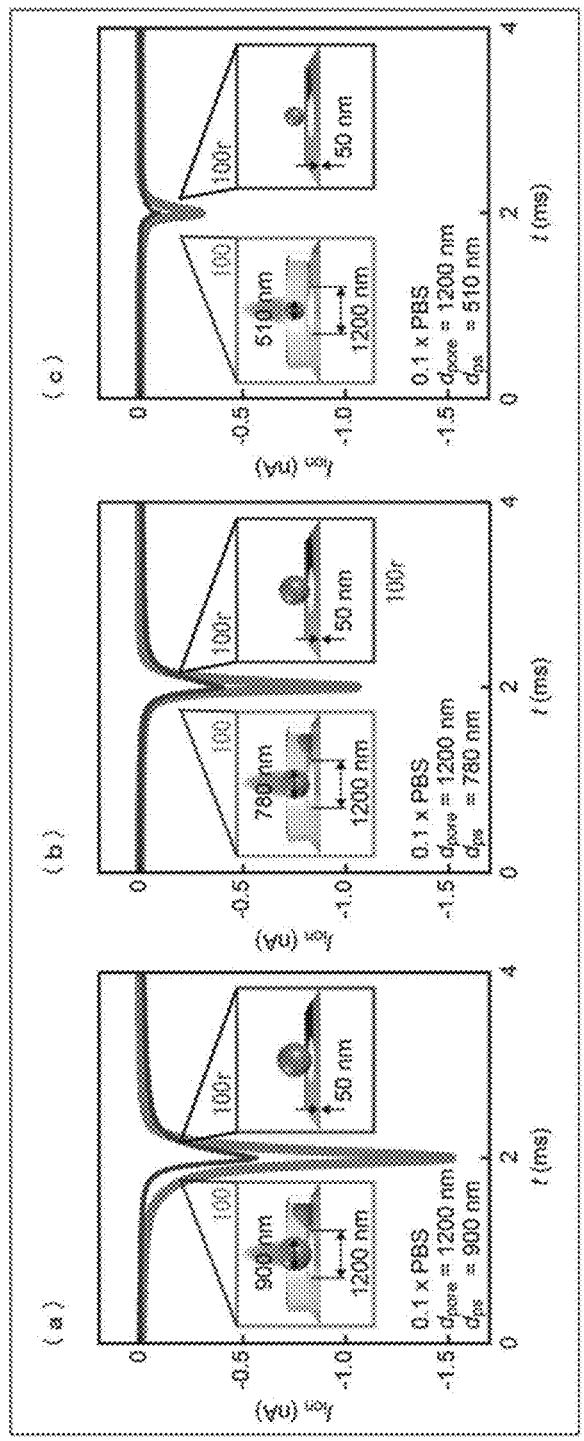
FIGS. 5 (a) to 5 (c) are views showing a pulse waveform of an ion current obtained by each of a detection device of Comparative Example and a detection device of a first embodiment.

FIG. 5 is a graph showing the pulse waveform obtained by the above experiment. Specifically, FIGS. 5 (*a*) to (*c*) show the pulse waveforms observed when the dps is 900 nm, 780 nm, and 510 nm, respectively. Hereinafter, a pulse height of the pulse waveform is referred to as Ip, and a pulse width of the pulse waveform is referred to as td. The Ip corresponds to an absolute value of a peak value of the Iion. The td corresponds to a length of time where the Ip is a nonzero value. It can also be said that the td is the time during which the particles P are present in the flow passage.

In all of the cases of FIGS. 5 (*a*) to (*c*), it was confirmed that the detection device 100 had a sufficiently larger Ip than the case of the detection device 100*r*. It was also confirmed that in the case of the detection device 100, the td was substantially the same as or slightly larger than that in the case of the detection device 100*r*. That is, it can be said that in the case of the detection device 100, the change of the Iion over time is more rapid than that in the case of the detection device 100*r*. Thus, the inventors confirmed that the response rate of the Iion could be sufficiently improved as compared with the detection device 100*r* by applying the configuration of the detection device 100 (more specifically, the flow passage 10).

(Further Examination for Response Rate of Ion Current)

Figure 6:
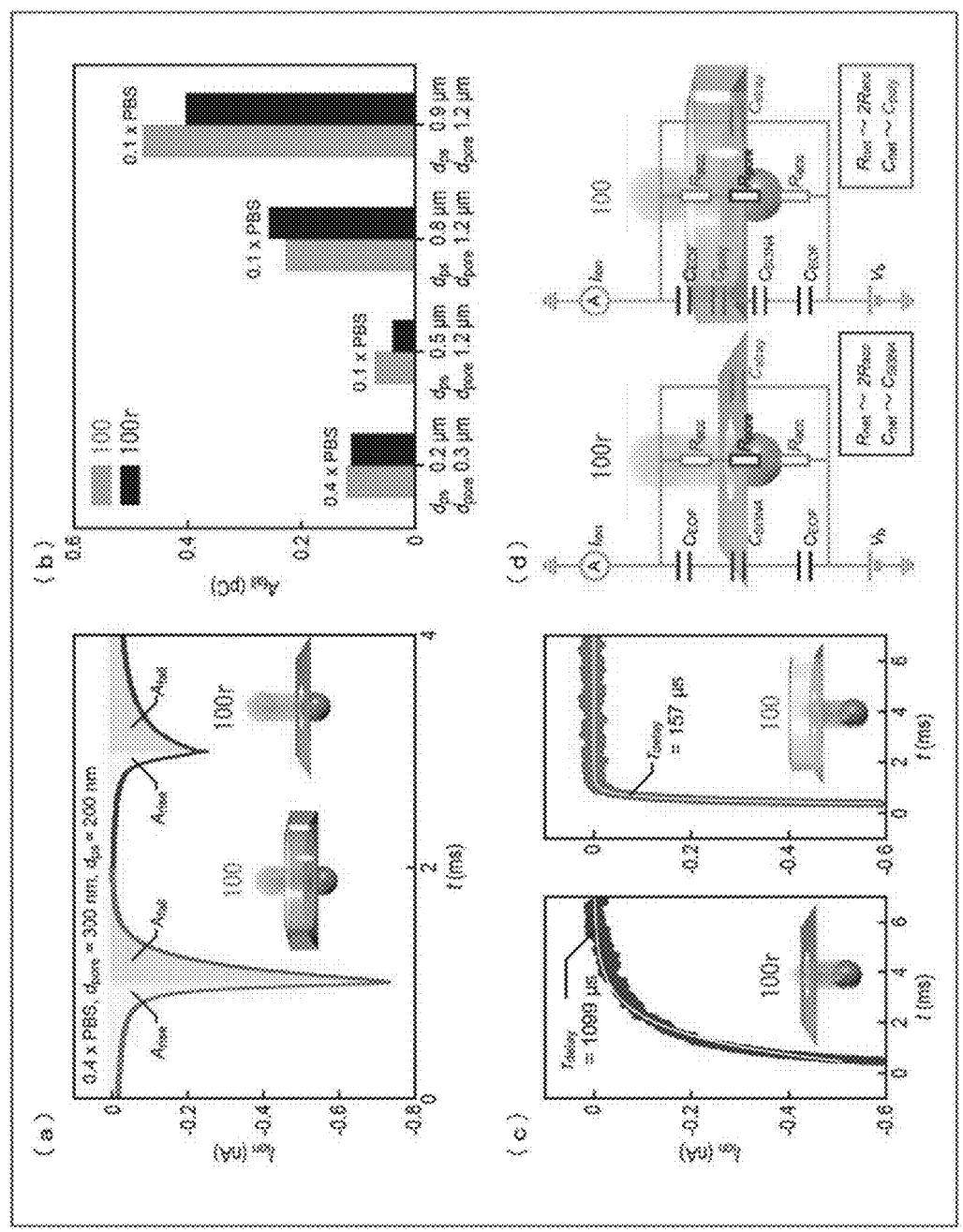
FIGS. 6 (a) to 6 (d) are views for explaining a difference in a response speed of an ion current between a detection device of Comparative Example and a detection device of a first embodiment.

The inventors further examined a difference in the response rate of the ion current between the detection device 100*r* and the detection device 100. FIG. 6 is a view for explaining these examinations.

<Additional Examination 1>

The inventors averaged a plurality of pulses (e.g., several hundred pulses) obtained in each of the detection device 100*r* and the detection device 100. The inventors compared the averaged pulses for the detection device 100*r* and the detection device 100.

FIG. 6 (*a*) shows the averaged pulse obtained in each of the detection device 100*r* and the detection device 100. In the experiment as shown in FIG. 6 (*a*), 0.4×PBS was used as a diluent. Further, the C (dpore) was set to 300 nm and the dps was set to 200 nm.

The inventors calculated Arise=Σ(Iion×Δt) in a rise portion of the averaged pulse (a portion where the Iion moves from 0 to a peak value over time). Further, the inventors calculated Afall=Σ(Iion×Δt) in a tail portion of the averaged pulse (a portion where the Iion moves from the peak value to 0 over time). It should be noted that the Δt is $10^{-6}$ (s). FIG. 6 (a) shows the Arise and the Afall for the averaged pulse in each of the detection device 100r and the detection device 100.

As shown in FIG. 6 (a), it was confirmed that there was a significant difference between the Arises of the detection device 100r and the detection device 100. This can also indicate that the response rate of the Iion is improved by the configuration of the detection device 100.

<Additional Examination 2>

The inventors varied experimental conditions and compared the Afalls for the detection device 100r and the detection device 100. FIG. 6 (b) shows comparison results of the Afalls obtained under various experimental conditions. FIG. 6 (b) shows Afalls obtained under the following four experimental conditions:

(1) diluent: 0.4×PBS, dps=0.2 μm, dope=0.3 μm;
(2) diluent: 0.1×PBS, dps=0.5 μm, dope=1.2 μm;
(3) diluent: 0.1×PBS, dps=0.8 μm, dpore=1.2 μm; and
(4) diluent: 0.1×PBS, dps=0.9 μm, dpore=1.2 μm.

As shown in FIG. 6 (b), it was confirmed that under any of the above experimental conditions (1) to (4), the Afalls do not differ so much between the detection device 100r and the detection device 100 (the error is at most about 5%). Based on this, the inventors presumed that values of Rnet (as described later) does not differ so much between the detection device 100r and the detection device 100.

<Additional Examination 3>

The inventors compared modes of changes of tail waveforms of pulses over time for the detection device 100r and the detection device 100. More Specifically, the inventors calculated a time constant (hereinafter, Tdelay) of the tail waveform by fitting the tail waveform by an exponential function. It should be noted that the Tdelay can also be expressed as a time constant of a RC circuit as described below. Therefore, the relationship: Tdelay=Rnet×Cnet is established. The Cnet will be described later.

FIG. 6 (c) shows the waveform fitted with the tail waveform for each of the detection device 100r and the detection device 100. As shown in FIG. 6 (c), for the detection device 100r, the Tdelay was calculated as 1099 μs. On the other hand, for the detection device 100, the Tdelay was calculated as 157 μs.

Thus, according to the detection device 100, it was confirmed that the Tdelay was sufficiently reduced as compared with the detection device 100r. Based on this, it can be said that the response rate of the Iion is improved by the configuration of the detection device 100. Furthermore, the inventors presumed that the Cnet was sufficiently reduced for the detection device 100 as compared with the detection device 100r based on the tendency of the Tdelay to decrease.

<Additional Examination 4>

The inventors examined an equivalent circuit (more strictly, a simple equivalent circuit) at the flow passage and its vicinity for each of the detection device 100r and the detection device 100. FIG. 6 (d) shows the equivalent circuit in the detection device 100r (hereinafter, referred to as an equivalent circuit of Comparative Example) and an equivalent circuit in the detection device 100 (hereinafter, referred to as an equivalent circuit of Example). Hereinafter, the electric resistance is simply referred to as a resistance.

Each symbol in FIG. 6 (d) is as follows:
CEOF: capacitance of electric double layer;
Cstray: stray capacitance;
$CSi_3N_4$: capacitance of substrate 1 ($Si_3N_4$ membrane);
Cpoly: capacitance of covering member 2 (polyimide layer);
Rpore: resistance of HL1 (nanopore); and
Racc: resistance other than HL1.

In the following examination, the Cstray will be ignored for simplicity. In each equivalent circuit of FIG. 6 (d), the combined resistance is represented as Rnet and the combined capacitance is represented as Cnet.

Hereinafter, the capacitance of the substrate 1 and the capacitance of the covering member 2 will be referred to as a substrate capacitance and a covering member capacitance, respectively. The $CSi_3N_4$ and Cpoly are examples of the substrate capacitance and the covering member capacitance, respectively. As described below, in the flow passage according to one aspect of the present disclosure, the covering member is arranged onto the substrate such that the substrate capacitance and the covering member capacitance are connected in series. The covering member capacitance is set to be lower than the substrate capacitance.

As shown in FIG. 6 (d), both of the equivalent circuit of Comparative Example and the equivalent circuit of Example have a common connection relationship of the resistance components. More Specifically, "one Rpore" and "two Raccs" are connected in series. Therefore, the following equation is established:

$$Rnet=Rpore+2\times Racc \qquad (1).$$

In general, the Racc is sufficiently larger than the Rpore, so Rnet≈2×Racc.

However, the connection relationship of the capacitance components is different between the equivalent circuit of Comparative Example and the equivalent circuit of Example. First, in the equivalent circuit of Comparative Example, "one $CSi_3N_4$" and "two CEOFs" are connected in series. Therefore, in the equivalent circuit of Comparative Example, the following relationship is established:

$$1/Cnet=(1/CSi_3N_4)+1/(2\times CEOF) \qquad (2).$$

In general, the CEOF is sufficiently lower than $CSi_3N_4$, so in the equivalent circuit of Comparative Example, Cnet≈$CSi_3N_4$. Hereinafter, the Cnet in Comparative Example is also referred to as Cnet (Comparative Example).

On the other hand, in the equivalent circuit of Example, "one $CSi_3N_4$", "one Cpoly", and "two CEOFs" are connected in series. That is, the Cpoly is further connected in series to the capacitance components in the equivalent circuit of Comparative Example. Therefore, in the equivalent circuit of Example, the following relationship is established:

$$1/Cnet=\{1/Cnet(1/Cnet(Comparative\ Example))\}+(1/Cpoly) \qquad (3).$$

As shown in FIG. 1 as described above, the size of the covering member 2 is sufficiently larger than that of the substrate 1. Therefore, the Cpoly can be regarded as being sufficiently smaller than $CSi_3N_4$(≈Cnet (Comparative Example)). Therefore, in the equivalent circuit of Example, Cnet≈Cpoly. Hereinafter, the Cnet in Example will also be referred to as Cnet (Example).

As described above, Cnet (Comparative Example) ≈$CSi_3N_4$ and Cnet (Example)≈Cpoly. That is, according to the equivalent circuit of Example, the Cnet can be sufficiently smaller than that of the equivalent circuit of Comparative Example. This is because, in the equivalent circuit of Example, the Cpoly among the three capacitances connected in series will be a dominant component that determines the capacitance of the Cnet.

As an example, the inventors calculated CSi₃N₄ based on Tdelay in the detector 100r. As a result, it was CSi₃N₄≈45 nF. In the calculation, the inventors used a value of Racc calculated based on an electrical resistivity ρ (known) of the medium.

Further, the inventors regarded the covering member 2 as a flat plate capacitor to calculate the Cpoly. More specifically, the inventors used the following relational expression:

$$Cpoly = \varepsilon 0 \times \varepsilon poly \times S/d \quad (4)$$

to calculate the Cpoly. As a result, it was Cpoly≈90 pF. In the equation (4), the ε0 is a permittivity of vacuum, and the εpoly is a relative permittivity of polyimide. The εpoly is 3.4. Further, the S is an area of a portion that is in contact with the medium, among the main surfaces of the covering member 2. The d is a thickness of the covering member 2 (that is, A in FIG. 1 as described above). The d is 5 μm.

In view of the foregoing, Cnet (Example)/Cnet(Comparative Example)≈90 pF/45 nF=0.002. As described above, the inventors confirmed that the equivalent circuit of Example could sufficiently reduce the Cnet as compared with the equivalent circuit of Comparative Example.

(Effect)

As described above, the detection device 100r (conventional nanopore sensor) did not lead to sufficient reduction of the current noise. Therefore, it is difficult for the detection device 100r to detect the particle P having a smaller size. This is because, in general, the smaller the size of the particle P, the lower the pulse height of the Iion, so that the influence of the current noise becomes more remarkable.

Furthermore, the detection device 100r did not lead to sufficient improvement of the response rate of the ion current. Therefore, it is difficult for the detection device 100r to detect the particle P with high time resolution. For example, it is difficult for the detection device 100r to detect the particle P moving at high speed in the flow passage. Thus, it was difficult for the detection device 100r to detect the particle P with sufficiently high sensitivity.

On the other hand, according to the detection device 100, unlike the detection device 100r, the current noise can be sufficiently reduced. Further, according to the detection device 100, the response rate of the ion current can be sufficiently improved. Therefore, according to the detection device 100, the detection accuracy of the particle P can be sufficiently improved as compared with the detection device 100r. For example, as shown in FIG. 4 described above, it was difficult for the detection device 100r to detect the particle P having a sufficiently small size (e.g., a nanoparticle having a diameter of about 100 nm) with high sensitivity. However, according to the detection device 100, the particle P can be detected with high sensitivity.

In particular, the detection device 100 can be provided with the covering member 2, so that the Cnet can be sufficiently decreased as compared with the detection device 100r. That is, the covering member 2 can sufficiently reduce the Tdelay. As a result, the response rate of the ion current can be sufficiently improved, as described above.

Further, as described below, according to the configuration of the flow passage 10, a resistance (hereinafter, Rpore2) of the HL2 (polyimide opening) is sufficiently lower than that of the Rpore. Therefore, even if the covering member 2 is provided, the Rnet in the equivalent circuit of Example is maintained at substantially the same value as the Rnet in the equivalent circuit of Comparative Example. That is, in FIG. 6 (*d*), it may be regarded as Rpore2≠0. Therefore, the Rpore2 is not shown in the equivalent circuit in FIG. 6 (*d*).

As described above, according to the covering member 2, the Cnet can be sufficiently reduced without substantially increasing the Rnet. That is, it is possible to sufficiently reduce the Tdelay (=Rnet×Cnet). Thus, the configuration of the flow passage 10 is particularly suitable for improving the response rate of the ion current. Therefore, the flow passage 10 is particularly suitable for the lower aspect ratio nanopore (nanopore configuration where the waveform of the ion current is complicated as compared with the higher aspect ratio nanopore).

(Examination of Dimensions of Each Portion of Flow Passage 10)

Subsequently, the inventors focused on electrical characteristics of the flow passage 10 and examined dimensions of each portion of the flow passage 10. Hereinafter, the relationship among A to C in FIG. 1 as described above will be examined. As described above, assuming that the electrical resistivity of the medium is ρ, the Rpore2 is expressed by:

$$Rpore2 = \rho \times A/\{(\pi \times B^2/4)\} + \rho/B \quad (5)$$

Here, if the second term on the right side of the equation (5) is ignored, it can be approximately expressed by:

$$Rpore2 = \rho \times \times A/\{(\pi \times B^2/4)\} \quad (6)$$

Further, the Rpore is expressed by:

$$Rpore = \rho \times D/\{(\pi \times C^2/4)\} + \rho/C \quad (7)$$

Here, in view of C>>D, the first term on the right side of the equation (7) can be ignored. Therefore, it can be approximately expressed by:

$$Rpore = \rho/C \quad (8)$$

As described above, the Rpore2 should be set to be sufficiently smaller than the Rpore. That is, the relationship among A to C is preferably set such that the relationship of Rpore2<<Rpore is satisfied.

(First Condition)

Based on the above points, the inventors have considered that the flow passage 10 is preferably formed such that the following condition (hereinafter, a first condition):

$$B \geq 10 \times C \quad (9)$$

For example, in the example of FIG. 1, since the B is 3 μm and the C is 300 nm, the B is equal to 10×C. That is, it satisfies the first condition.

As an example, a case of B=10×C is considered. Here, for the sake of simplicity, it is assumed that an approximation which ignores the first term on the right side of the equation (5) is established. In this case, it can be expressed by:

$$Rpore2 = \rho/B \quad (10)$$

In this case, Rpore2=ρ/(10×C)=Rpore/10. As described above, when the first condition is satisfied, the relationship: "Rpore2≤Rpore/10" (that is, 10×Rpore2≤Rpore) is established. Therefore, the Rpore2 can be set to be sufficiently smaller than the Rpore.

(Second Condition)

Furthermore, the inventors have considered that it is also preferable to form the flow passage 10 such that the following condition (hereinafter, a second condition) is satisfied:

$$B^2/A > 5 \times C \quad (11)$$

For example, in the example of FIG. 1, since the A is 5 μm, the ratio (B²/A) is 1.8 μm. On the other hand, 5×C is equal to 1.5 μm. That is, it satisfies the second condition.

As an example, a case of B²/A=5×C is considered. In this case, from the equation (6), it can be expressed by:

$$Rpore2 = \{4/(5\pi)\} \times (\rho/C) \quad (12)$$

When the equation (8) is substituted into the equation (12), Rpore2={4/(5×π)}×Rpore=0.25×Rpore.

As described above, when the second condition is satisfied, the relationship: "Rpore2<Rpore/4" (i.e., 4×Rpore2<Rpore) is established. In this case, the Rpore2 can be set to be sufficiently smaller than the Rpore. It is particularly preferable that the flow passage 10 is formed such that both the first condition and the second condition are satisfied.

As described above, in the flow passage 10, the Rpore2 is set to be smaller than the Rpore. Preferably, the Rpore2 is less than ¼ of the Rpore. More preferably, the Rpore2 is 1/10 or less of the Rpore.

(Example of Method for Producing Flow Passage 10)

Hereinafter, an example of a method for producing the flow passage 10 (the substrate 1 and the covering member 2) will be briefly described. However, one aspect of the present invention is not limited to the following examples, and known film forming techniques, lithography techniques, and etching techniques may be used.

<Producing Step of Substrate 1>

First, a layer of $Si_3N_4$ ($Si_3N_4$ membrane) having a thickness of 50 nm (=D) was formed using CVP (Chemical Vapor Deposition). Subsequently, electron beam lithography was used to form an opening (i.e., HL1) having a diameter of 300 nm (=C) in the $Si_3N_4$ membrane. The substrate 1 (the $Si_3N_4$ membrane provided with HL1) was thus obtained.

<Producing Step of Covering Member 2>

A photosensitive polyimide layer having a thickness of 5 μm (=A) was then formed on the surface of the substrate 1. The photosensitive polyimide layer was then irradiated with UV (Ultra Violet) light to form an opening (i.e., HL2) having a diameter of 3 μm (=B) in the photosensitive polyimide layer. The covering member 2 (polyimide layer provided with HL2) was thus obtained. That is, the flow passage 10 was produced.

[Variations]

In the first embodiment, the $Si_3N_4$ was illustrated as the material of the substrate 1. However, the material of the substrate 1 is not limited to this material. Another example of the material of the substrate 1 can include $SiO_2$.

Further, in the first embodiment, the polyimide has been illustrated as the material of the covering member 2. However, the material of the covering member 2 is not limited to this material. Another example of the covering member 2 can include PMMA (polymethylmethacrylate) or PDMS (polydimethylsiloxane).

Further, the inventors assumed that "the material of the covering member 2 may be a material having a relatively low relative permittivity" based on the concept of "reducing the Cnet by providing the covering member 2". For example, the material of the covering member 2 is not limited to the above examples, and a known polymer material can be used. Alternatively, a known inorganic material (more specifically, a non-metallic material) can be used as the material of the covering member 2.

As described above, in the flow passage according to one aspect of the present invention, the covering member capacitance is lower than the substrate capacitance. Therefore, the relative permittivity of the covering member (hereinafter, the covering member relative permittivity) is preferably lower than the relative permittivity of the substrate (hereinafter, the substrate relative permittivity). The εpoly (relative permittivity of polyimide) in the first embodiment is an example of the covering member relative permittivity. As described above, the εpoly is 3.4. On the other hand, the relative permittivity of the $Si_3N_4$ membrane (substrate) is $εSi_3N_4$=7.5. The $εSi_3N_4$ is an example of the substrate relative permittivity.

Second Embodiment

Figure 7:
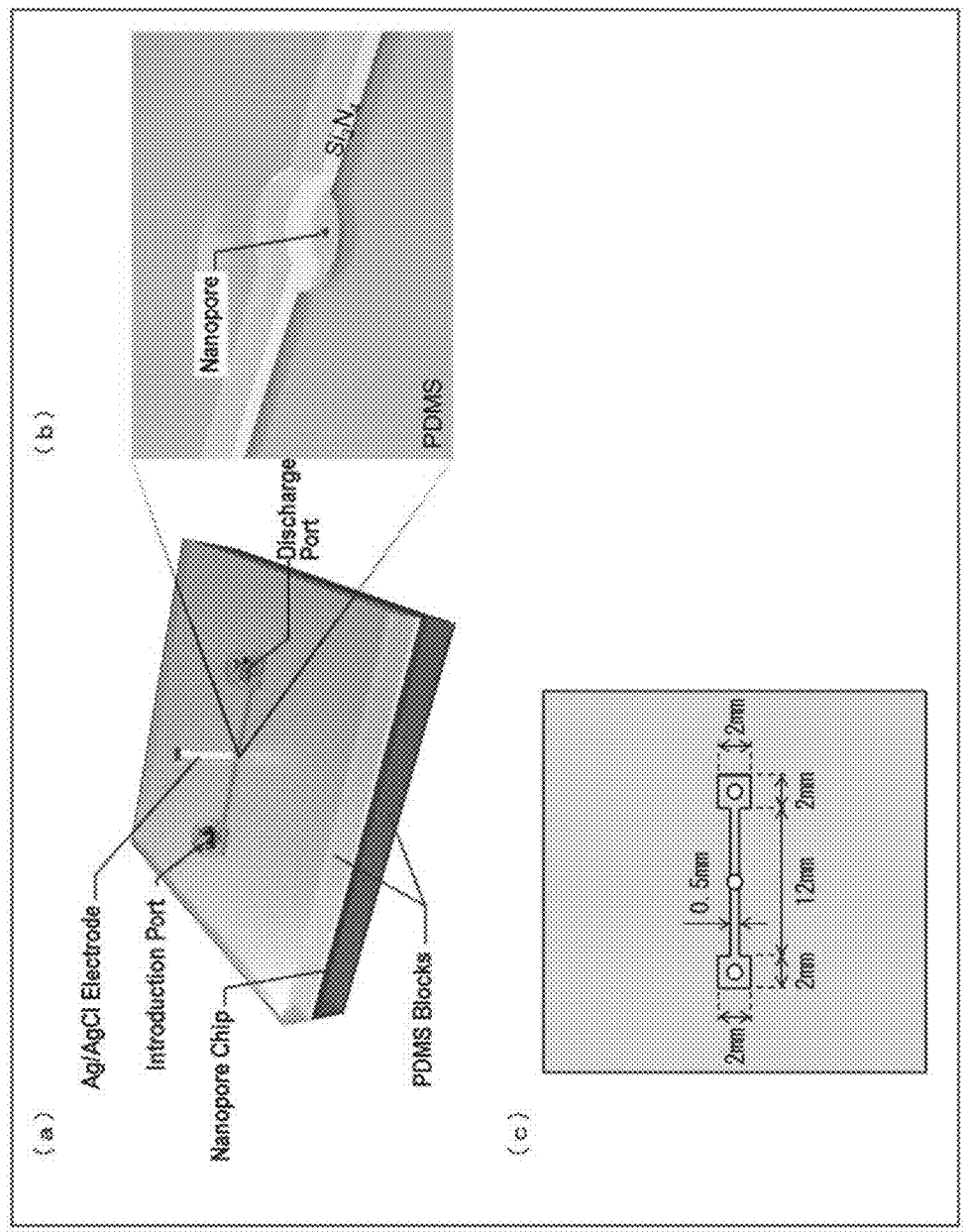
FIGS. 7 (a) to 7 (c) are views for explaining a configuration of a detection device of a second embodiment.

FIG. 7 is a view for explaining a configuration of a detection device according to a second embodiment. Unlike the detection device 100 of the first embodiment, the detection device of the second embodiment includes an auxiliary flow passage (e.g., a micro flow passage) for moving the particle P to the vicinity of the flow passage according to one aspect of the present invention. Hereinafter, the detection device of the second embodiment is simply referred to as a "detection device". Further, the flow passage of the second embodiment is simply referred to as a "flow passage".

Specifically, FIG. 7 (a) shows the overall configuration of the detection device. FIG. 7 (b) is an enlarged view of the nanopore and its vicinity in FIG. 7 (a). FIG. 7 (b) shows the structure of the flow passage. FIG. 7 (c) shows a configuration of a nanopore chip provided in the detection device.

As shown in FIG. 7 (a), the detection device includes: Ag/AgCl electrodes (first electrode/second electrode); a nanopore chip (substrate); and PDMS blocks (covering layers). The nanopore chip is provided with a nanopore (HL1), an introduction port, and a discharge port. The nanopore chip is also provided with a flow passage that communicates the nanopore with the introduction port and the discharge port (also see FIG. 7 (c)). The nanopore chip is made of $Si_3N_4$. The PDMS block is provided with HL2 (see FIG. 7 (b)). The two PDMS blocks are arranged so as to sandwich the nanopore chip.

As an example, a user introduces a liquid (suspension) containing the particles P into the introduction port. Once the fluid reaches the vicinity of the nanopore through the auxiliary flow passage, the particles P can be moved using the flow passage as described above. Therefore, the liquid from which a part of the particles P has been removed is directed to the discharge port. The liquid is discharged through the discharge port.

<Additional Examination>

The inventors confirmed the following matters:
(1) when only a part of the surface of the nanopore chip is covered with the covering layer (e.g., PMMA), the effect of reducing the Cnet is not so high; and
(2) on the other hand, when only the back surface of the nanopore chip is covered with the covering layer, the effect of reducing the Cnet is higher.

Based on this, the inventors considered that the capacitance derived from the surface of the nanopore chip that was in contact with the liquid might significantly contribute to the "RC effect", in other words, "the magnitude of Tdeli (=Rnet×Cnet)" (which may be expressed as a degree of blunted waveform of the ion current).

Third Embodiment

The inventors conducted further examination for "Additional Examination 1" in the second embodiment. In the third embodiment, an example of the examination results will be described.

Figure 8:
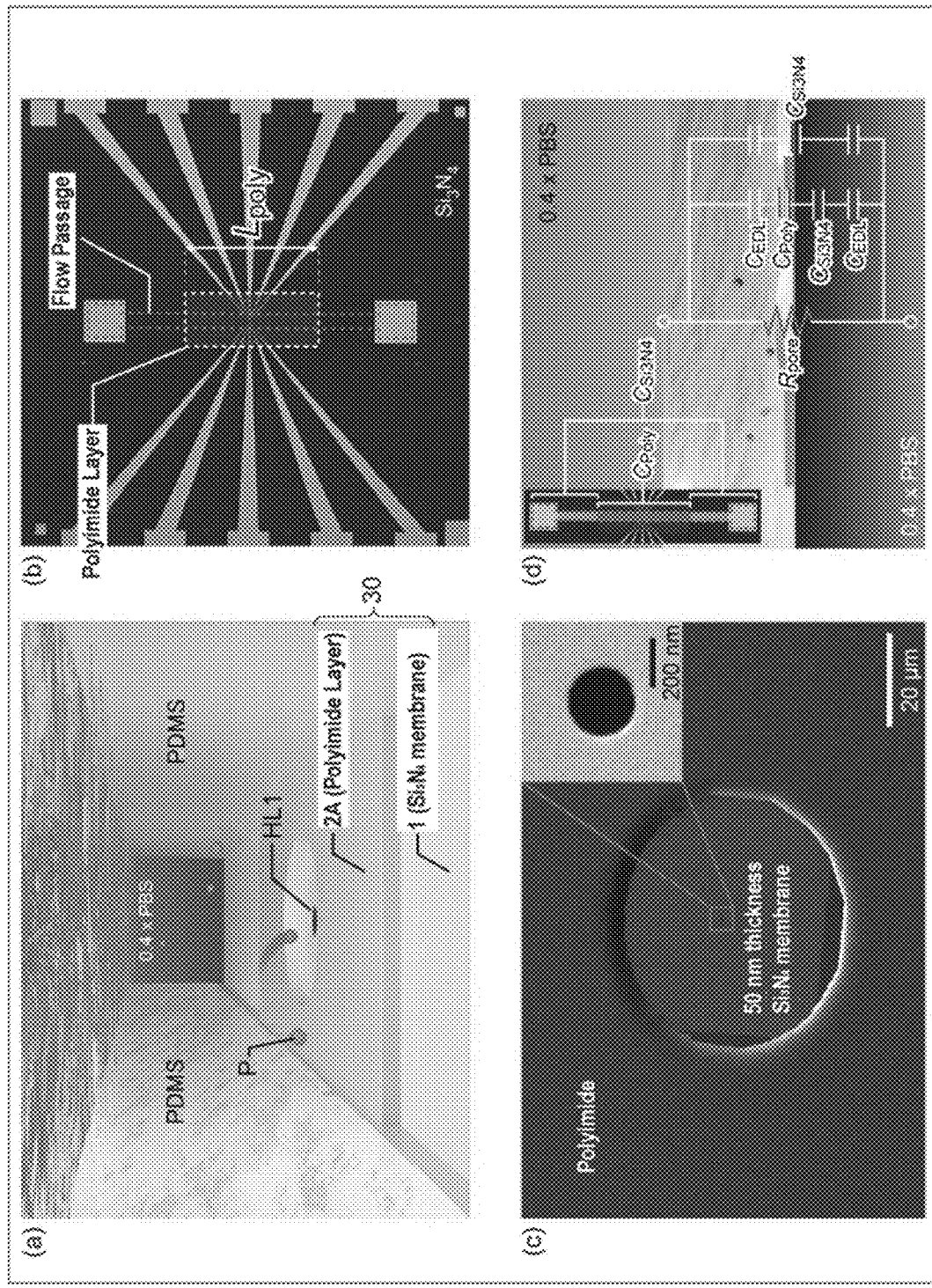
FIGS. 8 (a) to 8 (d) are views for explaining a flow passage of a third embodiment.

FIG. 8 is a view for explaining a flow passage 30 of the third embodiment. FIG. 8 (a) schematically shows the configuration of the flow passage 30 and its vicinity. The flow passage 30 includes a polyimide layer as a covering member, as with the flow passage 10 of the first embodiment. Hereinafter, the covering member of the flow passage 30 will be referred to as a covering member 2A. The covering member 2A is provided on an upper surface of the substrate 1 ($Si_3N_4$ membrane), as with the covering member 2. In the detection device of the third embodiment, a flow passage (PDMS channel) defined by PDMS is provided as in the second embodiment.

In the third embodiment, the inventors examined a case of dps=200 nm. In the third embodiment, the covering member 2A is formed with B=50 μm. That is, in the third embodiment, the B is set to be larger than that of the first embodiment. In the third embodiment, 0.4×PBS is used as a diluent. Other conditions are the same as those in the first embodiment unless otherwise specified.

FIG. 8 (b) shows an optical image of the nanopore chip (substrate 1) covered with the polyimide layer (covering member 2A). The Lpoly represents a length of the covering member 2A in the longitudinal direction. In the third embodiment, the y direction is the longitudinal direction of the flow passage 30 in the horizontal plane (xy plane). The y direction corresponds to, for example, the left-right direction in FIG. 1. On the other hand, the x direction is also referred to as a width direction. In the third embodiment, the x direction is a short direction of the flow passage 30 on the horizontal plane. Both of the longitudinal direction and the width direction are examples of the r direction as described above.

Further, as shown in FIG. 8 (b), the nanopore chip of the third embodiment is provided with the same flow passage as in FIG. 7 (c). As shown in FIGS. 8 (a) and 8 (b), the third embodiment mainly illustrates a case where only a part of the upper surface of the substrate 1 is covered with the covering member 2A.

FIG. 8 (c) shows an example of an SEM image of the flow passage 30. As shown in FIG. 8 (c), in the third embodiment, the HL1 is also sufficiently smaller than the HL2.

FIG. 8 (d) shows an equivalent circuit of the flow passage 30 and its vicinity. The CEDL in FIG. 8 (d) is a capacitance of the electric double layer. The CEDL corresponds to the CEOF in FIG. 6 (d). In the equivalent circuit in FIG. 8 (d), the Cpoly and the $CSi_3N_4$ are connected in series at a portion where the substrate 1 is covered with the covering member 2A. In addition, the $CSi_3N_4$ at the right end of the equivalent circuit in FIG. 8 (d) shows the substrate capacitance at a portion where the substrate 1 is not covered with the covering member 2A.

As with the first embodiment, the CEDL is sufficiently smaller than the $CSi_3N_4$. Therefore, the CEDL will be ignored. Further, as with the first embodiment, the Cpoly is sufficiently smaller than the $CSi_3N_4$. Based on this, the Cnet in the equivalent circuit of FIG. 8 (d) can be approximately expressed by:

$$Cnet=Cpoly+CSi_3N_4 \qquad (13).$$

As described below, in Embodiment 3, each of the Cpoly and the $CSi_3N_4$ depends on the Lpoly. Therefore, the Cnet also depends on the Lpoly.

(Regarding Cpoly)

As shown in FIG. 7 (c), in the nanopore chip of the third embodiment, the length of the flow passage in the longitudinal direction, which excludes two square end portions, is 12 mm. Therefore, first, a case of Lpoly 12 mm is considered. In this case, the Cpoly can be expressed by:

$$Cpoly=\alpha \times wthin \times Lpoly \qquad (14A),$$

with $\alpha=\epsilon 0 \times \epsilon poly/tpoly$.

The wthin is a width of the flow passage in a region excluding the two end portions. As shown in FIG. 7 (c), the wthin is 0.5 mm. The tpoly is a thickness of the polyimide layer (covering member 2A) and corresponds to the A in FIG. 1. As with the first embodiment, the tpoly is 5 μm.

Next, a case of Lpoly>12 mm is considered. In this case, the Cpoly can be expressed by:

$$Cpoly=0.012\times\alpha\times wthin+(Lpoly-0.012)\times\alpha\times wsq \qquad (14B).$$

The wsq represents a width of each of the square ends of the flow passage. As shown in FIG. 7 (c), the wsq is 2 mm. Therefore, the total length of the flow passage in the longitudinal direction is 16 mm. Based on this point, in the third embodiment, the maximum value of the Lpoly is 16 mm.

(Regarding $CSi_3N_4$)

First, a case of Lpoly≤12 mm is considered. In this case, the $CSi_3N_4$ is expressed by:

$$CSi_3N_4=(0.012-Lpoly)\times\beta \qquad (15A),$$

with $\beta=\epsilon 0 \times \epsilon Si_3N_4 \times wthin/tSi_3N_4$.

Further, the $tSi_3N_4$ is a thickness of the substrate 1 and corresponds to the D in FIG. 1. As with the first embodiment, the $tSi_3N_4$ is 50 nm. As described above, $tSi_3N_4 \ll tpoly$.

On the other hand, in the case of Lpoly>12 mm, the $CSi_3N_4$ is expressed by:

$$CSi_3N_4=(Lpoly-0.012)\times\beta \qquad (15B).$$

Based on the equations (13) to (15B), the inventors predicted that the Cnet tended to decrease as the Lpoly increased.

Examination 1 in Third Embodiment

Figure 9:
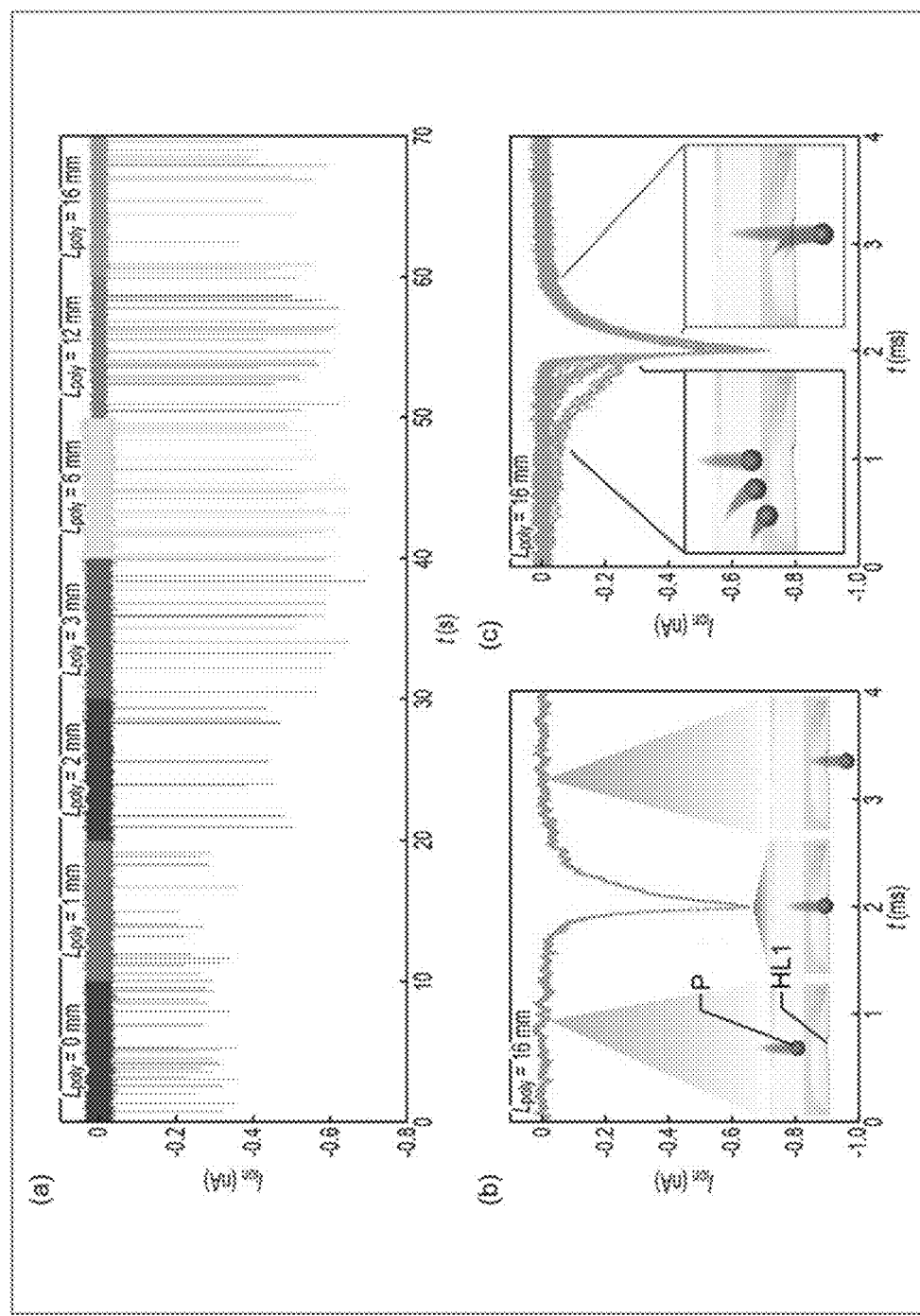
FIGS. 9 (a) to 9 (c) are views for explaining one examination result in a third embodiment.

FIG. 9 is a view for explaining one examination result in the third embodiment. The inventors conducted experiments with various different Lpoly values. More particularly, the inventors conducted experiments on the following seven cases:

(Case 1) Lpoly=0 mm;
(Case 2) Lpoly=1 mm;
(Case 3) Lpoly=2 mm;
(Case 4) Lpoly=3 mm;
(Case 5) Lpoly=6 mm;
(Case 6) Lpoly=12 mm; and
(Case 7) Lpoly=16 mm.

The case 1 corresponds to the case where the covering member 2A is not provided. That is, the case 1 corresponds to Comparative Example of the first embodiment.

FIG. 9 (a) shows the waveform of the Iion in each of the above seven cases. As shown in FIG. 9 (a), it was confirmed that the Ip (the absolute value of the peak value of the Iion) tended to increase as the Lpoly increased. Further, in the cases 6 and 7, it was confirmed that the current noise could be particularly effectively reduced. Therefore, for example, the Lpoly is preferably set to 12 mm or more.

Further, FIG. 9 (b) shows one pulse waveform of the Iion for the case 7. In FIG. 9 (c), thirty pulse waveforms of the Iion for Case 7 are shown in a superimposing manner.

In the example of FIG. 9 (c), the shape of the rise portion of the pulse has a relatively large variation for each pulse. It is believed that the large variation in the rise portion is caused by the particle P intruding into an inlet portion (HL2 located at the upper portion) of the flow passage 30 due to various incident angles. On the other hand, the shape of the tail portion of the pulse has a relatively small variation for each pulse. It is believed that the small variation in the tail portion is caused by substantially uniform alignment of the traveling directions of the particle P that have passed through the HL1, at an outlet portion (lower portion) of the flow passage 30.

Examination 2 in Third Embodiment

Figure 10:
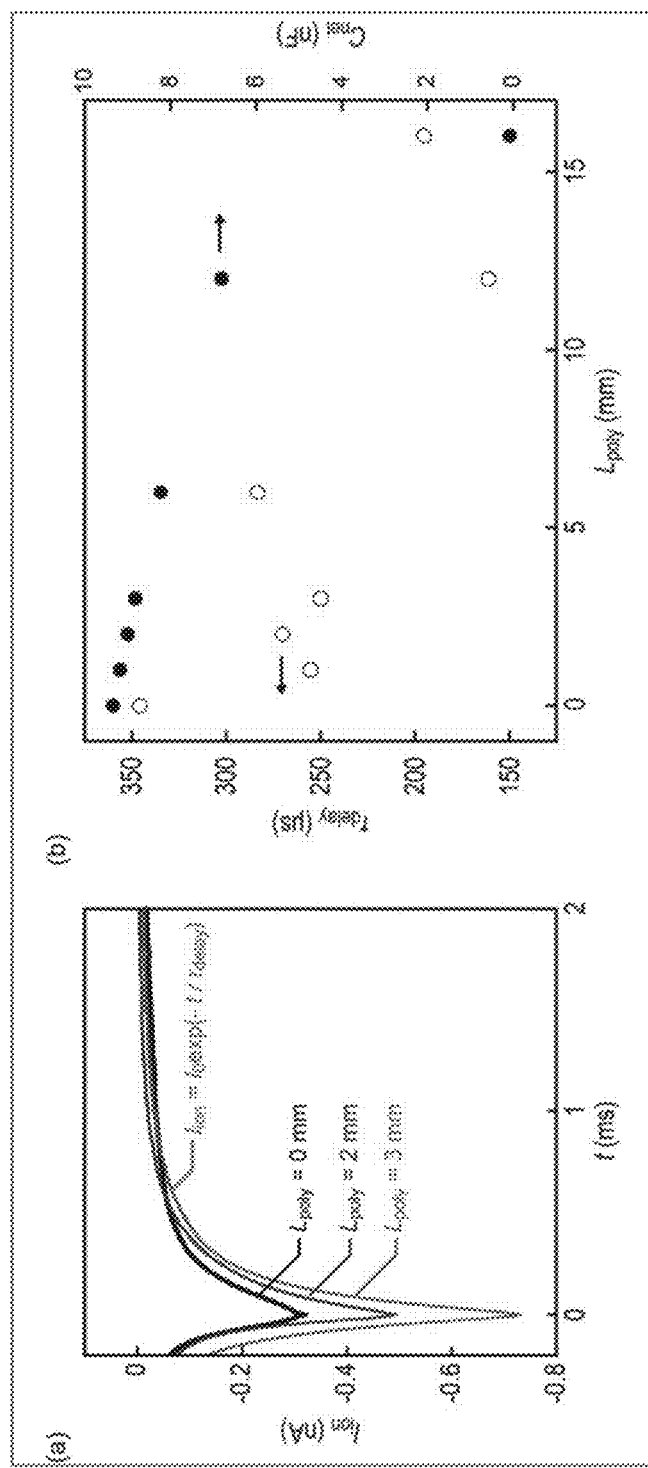
FIGS. 10 (a) and (b) are views for explaining another examination result in a third embodiment.

FIG. 10 is a view for explaining other examination result in the third embodiment. FIG. 10 (a) shows an averaged pulse for each of the cases 1, 3, and 4. It was also confirmed from FIG. 10 (a) that the Ip tended to increase as the Lpoly increased.

Further, as understood from the first embodiment, the Iion at the tail portion can be expressed by:

$$\text{Iion}=I0 \times \exp(-t/T\text{delay}) \quad (16).$$

That is, the tail waveform can be fitted by the equation (16). The I0 is a peak value of the Iion. FIG. 10 (a) shows a tail waveform calculated based on the equation (8) for the case of Lpoly=3 mm. It was confirmed that the tail waveform substantially coincided with the tail waveform of the averaged pulse for the case 4.

Subsequently, the inventors identified Tdelay for each of the cases 1 to 7 using the equation (8). In FIG. 10 (b), the Tdeliy for each of the cases 1 to 7 is represented by the white circle (for the value of the Tdelay, see the vertical axis at the left end of the graph in the same figure). Further, in FIG. 10 (b), the Cnet calculated based on the equations (13) to (15B) for each of the cases 1 to 7 is represented by the black circle (for the value of the Cnet, see the vertical axis at the right end of the graph in the same figure).

As described above, FIG. 10 (b) shows dependency of the Tdelay and the Cnet on the Lpoly (the horizontal axis of the graph in the same figure). As shown in FIG. 10 (b), it was confirmed that the Tdelay tended to decrease as the Lpoly increased. Further, it was confirmed that the Cnet tended to decrease as the Lpoly increased.

However, there is a slight difference between (i) the decreasing tendency of the Tdelay with the increase of the Lpoly and (ii) the decreasing tendency of the Cnet with the increase of Lpoly. The difference would be due to various noises. As described above, when the Lpoly is smaller, the noise would be larger. Therefore, it can be preferable that the Lpoly is set to a value that is large to some extent. For example, as described above, the Lpoly is preferably set to 12 mm or more.

Fourth Embodiment

The inventors conducted further examination on the "Additional Examination 2" in the second embodiment. In the fourth embodiment, an example of the examination result will be described.

Figure 11:
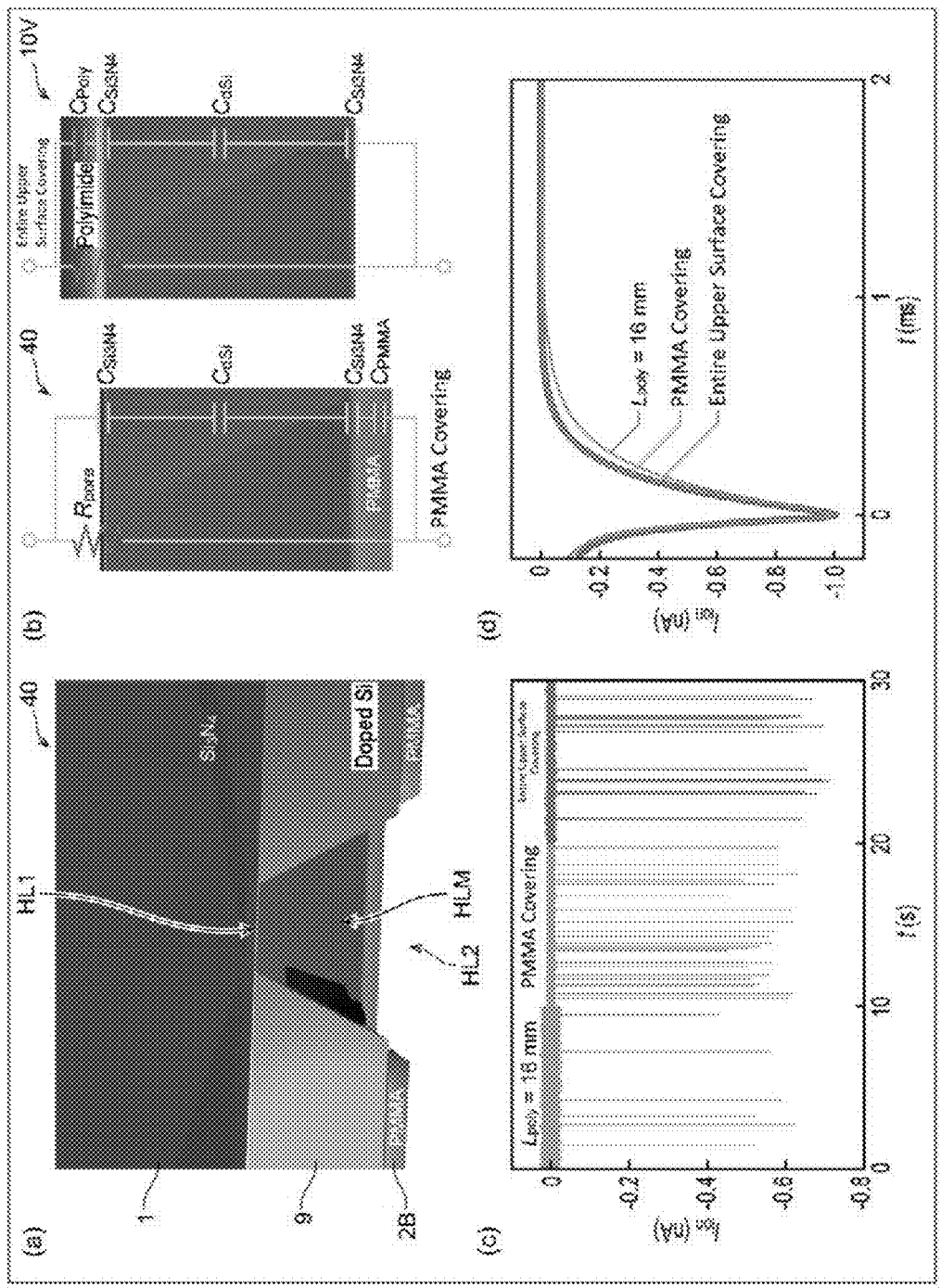
FIGS. 11 (a) to 11 (d) are views for explaining a flow passage of a fourth embodiment.

FIG. 11 is a view for explaining a flow passage 40 of the fourth embodiment. FIG. 11 (a) schematically shows the configuration of the flow passage 40. The flow passage 40 is provided with a support member 9 on a lower surface of the substrate 1. The support member 9 supports the substrate 1. The support member 9 is a doped Si substrate, for example. The support member 9 is provided with a support member opening (hereinafter, HLM) at a position corresponding to the HL1. The HLM penetrates the support member 9 in the z direction. The HLM is provided such that the support member 9 does not cover the HL1.

Also, the flow passage 40 is provided with a covering member 2B on a lower surface of the support member 9. The covering member 2B is made of PMMA. Thus, unlike the first to third embodiments, the flow passage 40 is not provided with the covering member on the upper surface of the substrate 1. In the flow passage 40, the covering member 2B is provided below the substrate 1. As shown in FIG. 11 (a), the covering member 2B is in indirect contact with the substrate 1 via the support member 9. In the covering member 2B, the HL2 is provided at a position corresponding to the HL1 and the HLM.

In the configuration of the flow passage 40, the substrate capacitance and the covering member capacitance are also connected in series. As described above, in the flow passage according to one aspect of the present invention, the substrate and the covering member may be separated from each other in the z direction. In the flow passage according to one aspect of the present invention, a first surface (upper surface) of the substrate may be referred to as a surface that is not in contact with the support member 9, among the two main surfaces of the substrate. Further, a second surface (lower surface) of the substrate may be referred to as a surface in contact with the support member 9 (a surface supported by the support member 9), among the two main surfaces of the substrate.

FIG. 11 (b) shows an equivalent circuit of the flow passage 40 and its vicinity. FIG. 11 (b) also shows a flow passage 10V for comparison with the flow passage 40. FIG. 11 (b) further shows an equivalent circuit of the flow passage 10V and its vicinity. In the flow passage 10V, the support member 9 in the flow passage 10 is explicitly shown. As with the flow passage 10, in the flow passage 10V, the entire upper surface of the substrate 1 except for the vicinity of the HL is covered with the polyimide layer (covering member 2). Hereinafter, such a covering manner is referred to as "the entire upper surface covering". In the flow passage 10V, the covering member 2 is in direct contact with the substrate 1 without interposing the support member 9.

On the other hand, in the flow passage 40, the covering member 2B is provided at a position corresponding to a part of the lower surface of the substrate 1. Hereinafter, such a covering manner is referred to as "PMMA covering". As shown in the third embodiment, the inventors have found that the entire upper surface covering is not essential in the flow passage according to one aspect of the present invention as a new finding. The configuration of the flow passage 40 has been created by the inventors based on the new finding.

In the equivalent circuit in FIG. 11 (b), the CPMMA is a capacitance of the covering member 2B. The CPMMA is another example of the covering member capacitance. The CdSi is a capacitance of the support member 9. The CdSi is sufficiently larger than the CPMMA and the $CSi_3N_4$. Therefore, the CdSi may be ignored in the calculation of the Cnet.

In each equivalent circuit in FIG. 11 (b), the substrate capacitance and the covering member capacitance are also connected in series. In the example of FIG. 11 (b), the CPMMA≈44 pF. Therefore, in the equivalent circuit of the flow passage 40, Cnet≈44 pF. On the other hand, the $CSi_3N_4$ is 13 nF. Therefore, in the equivalent circuit of the flow passage 10V, Cnet≈13 nF. Thus, the inventors have found that the PMMA covering can further reduce the covering member capacitance as compared with the entire upper surface covering. That is, the flow passage 40 can allow a smaller Cnet than that of the flow passage 10V to be obtained.

As described above, in the flow passage according to one aspect of the present invention, the covering member may be provided so as to overlap with a part of the substrate at a position excluding the HL2 as viewed from the z direction. That is, the covering member may not be provided so as to overlap with the entire substrate at the position excluding the HL2 as viewed from the z direction. Further, in the flow passage according to one aspect of the present invention, the covering member can also be provided below the substrate, thereby resulting in a higher degree of freedom in the structural design of the flow passage.

FIG. 11 (c) shows a waveform of the Iion for each of (i) "Lpoly=16 mm (the case 7 of the above third embodiment)", (ii) "PMMA covering (flow passage 40)", and (iii) "the entire upper surface covering (flow passage 10V)". The data for "Lpoly=16 mm" is shown for comparison with the data for "PMMA covering" and "the entire upper surface covering". It was confirmed that according to the PMMA covering, the current noise could be particularly effectively reduced as compared with the case 7 and the entire upper surface covering.

FIG. 11 (d) shows an averaged pulse in each of (i) "Lpoly=16 mm", (ii) "PMMA covering", and (iii) "the entire upper surface covering". As with the third embodiment, the inventors identified Tdelay for each of the PMMA covering and the entire upper surface covering.

As shown in FIG. 10, the Tdeli was about 200 μs for the case 7. On the other hand, the Tdelay was 145 μs for the PMMA covering. Further, the Tdelay was 149 μs for the entire upper surface covering. Thus, it was confirmed that a particularly small Tdelay can be obtained for the PMMA covering. In view of these, it is expected that the configuration of the flow passage 40 is particularly suitable for improving the response rate of the ion current.

[Supplement 1]

As described above, in the flow passage according to one aspect of the present invention, the covering member capacitance (hereinafter, C2) is set to be lower than the substrate capacitance (hereinafter, C1). For example, as shown in each of the above embodiments, the C2 takes a pF order value and the C1 takes a pF order value.

Therefore, as an example, the C2 is preferably 1/100 or less of the C1. If each capacitance is thus set, it can be said that C2<<C1. As will be understood from each of the above embodiments, when the C1 and the C2 are connected in series, the following relationship is established:

$$Cnet \approx (C1 \times C2)/(C1+C2) \quad (17).$$

Further, in a case of C2<<C1, it is:

$$Cnet \approx (C1 \times C2)/C1 = C2 \quad (17A)$$

Thus, by setting the C2 to be sufficiently smaller than the C1 (e.g., setting the C2 to 1/100 or less of the C1), the Cnet can be effectively reduced.

Supplement 2

In the flow passage according to one aspect of the present invention, the covering members may be provided both above and below the substrate.

CONCLUSION

The flow passage according to one aspect of the present invention is a flow passage provided in a nanopore sensor, the flow passage comprising: a substrate; and a covering member provided at a position corresponding to the substrate, wherein the substrate comprises a substrate opening that penetrates the substrate in a first direction, the first direction being a thickness direction of each of the substrate and the covering member, wherein the covering member comprises a covering member opening that penetrates the covering material in the first direction, wherein the covering member opening is provided such that the substrate opening is not covered with the covering member, wherein the covering member is arranged onto the substrate such that a substrate capacitance and a covering member capacitance are connected in series, the substrate capacitance being a capacitance of the substrate and the covering member capacitance being a capacitance of the covering member, and wherein the covering member capacitance is lower than the substrate capacitance.

In one embodiment according to the present invention, the flow passage satisfies a relationship: $B \geq 10 \times C$, wherein the B represents a maximum length of the covering member opening in a direction perpendicular to the first direction, and the C represents a maximum length of the substrate opening in the direction perpendicular to the first direction.

In an embodiment according to the present invention, the flow passage satisfies a relationship: $B^2/A > 5 \times C$, wherein the A represents a thickness of the covering member.

In the flow path according to an embodiment of the present invention, the covering member is made of a polymer material.

In the flow passage according to an embodiment of the present invention, the polymer material is polyimide, polymethylmethacrylate, or polydimethylsiloxane.

In the flow passage according to an embodiment of the present invention, the substrate is made of $Si_3N_4$ or $SiO_2$.

In the flow passage according to an embodiment of the present invention, the covering member has a relative permittivity lower than that of the substrate.

In the flow passage according to an embodiment of the present invention, the covering member opening has an electric resistance lower than that of the substrate opening.

In the flow passage according to an embodiment of the present invention, the electric resistance of the covering member opening is lower than 1/4 of that of the substrate opening.

In the flow passage according to an embodiment of the present invention, the electric resistance of the covering member opening is 1/10 or less of that of the substrate opening.

In the flow passage according to an embodiment of the present invention, the covering member overlaps with a part of the substrate at a position excluding the covering member opening as viewed from the first direction.

The flow passage according to an embodiment of the present invention further comprises a support member for supporting the substrate, and the covering member is in indirect contact with the substrate via the support member.

In the flow passage according to an embodiment of the present invention, the covering member is in direct contact with the substrate.

In the flow passage according to an embodiment of the present invention, the covering member capacitance is 1/100 or less of the substrate capacitance.

[Another Expression of One Aspect of Present Invention]

The flow passage according to an embodiment of the present invention is a flow passage provided in a nanopore sensor, the flow passage comprising: a substrate; and a covering member deposited on the substrate, wherein the substrate comprises a substrate opening that penetrates the substrate in a first direction, the first direction being a thickness direction of each of the substrate and the covering member, wherein the covering member comprises a covering member opening that penetrates the covering member in the first direction, wherein the covering member opening is provided such that the substrate opening is not covered with the covering member, and wherein the flow passage satisfies a relationship: B≥10×C, in which the B is a maximum length of the covering member opening in a direction perpendicular to the first direction and the C is a maximum length of the substrate opening in the direction perpendicular to the first direction.

In an embodiment according to the present invention, the flow passage satisfies a relationship: $B^2/A>5\times C$, wherein the A is a thickness of the covering member.

[Additional Notes]

One aspect of the present invention is not limited to each of the embodiments as described above, and various modifications may be made within the scope set forth in the claims. Embodiments obtained by combining the technical means disclosed in the different embodiments as needed are also included in the technical scope of one aspect of the present invention.

DESCRIPTION OF REFERENCE NUMERALS

1: substrate
2, 2A, 2B: covering member
9: support member
10, 10V, 30, 40: flow passage
100: detection device (nanopore sensor)
HL1: substrate opening (nanopore)
HL2: covering member opening (polyimide opening)
A: thickness of covering member
B: diameter of covering member opening (maximum width in cross section of covering member opening in direction perpendicular to first direction)
C: diameter of substrate opening (maximum width in cross section of substrate opening in direction perpendicular to first direction)
Z direction: thickness direction (first direction)
$C_{Si_3N_4}$: capacitance of $Si_3N_4$ membrane (substrate) (substrate capacitance)
Cpoly: capacitance of polyimide layer (covering member) (covering member capacitance)
CPMMA: capacitance of PMMA (covering member) (covering member capacitance)
Rpore: resistance of substrate opening (electrical resistance)
Rpore2: resistance of covering member opening (electrical resistance)

The invention claimed is:

1. A flow passage provided in a nanopore sensor, the flow passage comprising:
 a substrate; and
 a covering member provided at a position corresponding to the substrate;
 wherein the substrate comprises a substrate opening that penetrates the substrate in a first direction, the first direction being a thickness direction of each of the substrate and the covering member;
 wherein the covering member comprises a covering member opening that penetrates the covering material in the first direction;
 wherein the covering member opening is provided such that the substrate opening is not covered with the covering member;
 wherein the covering member is arranged onto the substrate such that a substrate capacitance and a covering member capacitance are connected in series, the substrate capacitance being a capacitance of the substrate and the covering member capacitance being a capacitance of the covering member; and
 wherein the covering member capacitance is lower than the substrate capacitance.

2. The flow passage according to claim 1, wherein the flow passage satisfies a relationship: B≥10×C, wherein the B represents a maximum length of the covering member opening in a direction perpendicular to the first direction, and the C represents a maximum length of the substrate opening in the direction perpendicular to the first direction.

3. The flow passage according to claim 1, wherein the flow passage satisfies a relationship: $B^2/A>5 \times C$, wherein the A represents a thickness of the covering member.

4. The flow path according to claim 1, wherein the covering member is made of a polymer material.

5. The flow passage according to claim 4, wherein the polymer material is polyimide, polymethylmethacrylate, or polydimethylsiloxane.

6. The flow passage according to claim 1, wherein the substrate is made of $Si_3N_4$ or $SiO_2$.

7. The flow passage according to claim 1, wherein the covering member has a relative permittivity lower than that of the substrate.

8. The flow passage according to claim 1, wherein the covering member opening has an electric resistance lower than that of the substrate opening.

9. The flow passage according to claim 8, wherein the electric resistance of the covering member opening is lower than 1/4 of that of the substrate opening.

10. The flow passage according to claim 9, wherein the electric resistance of the covering member opening is 1/10 or less of that of the substrate opening.

11. The flow passage according to claim 1, wherein the covering member overlaps with a part of the substrate at a position excluding the covering member opening as viewed from the first direction.

12. The flow passage according to claim 1, further comprising a support member for supporting the substrate,
 wherein the covering member is in indirect contact with the substrate via the support member.

13. The flow passage according to claim 1, wherein the covering member is in direct contact with the substrate.

14. The flow passage according to claim 1, wherein the covering member capacitance is 1/100 or less of the substrate capacitance.

15. The flow passage according to claim 2, wherein the flow passage satisfies a relationship: $B2/A>5 \times C$, wherein the A represents a thickness of the covering member.

16. The flow passage according to claim 2, wherein the covering member has a relative permittivity lower than that of the substrate.

17. The flow passage according to claim 3, wherein the covering member has a relative permittivity lower than that of the substrate.

18. The flow passage according to claim 15, wherein the covering member has a relative permittivity lower than that of the substrate.

* * * * *